(12) United States Patent  (10) Patent No.: US 8,170,890 B1
Lawlor  (45) Date of Patent: May 1, 2012

(54) METHOD OF INFERRING A HEALTH CONDITION BASED ON A PRESCRIPTION FILLED FOR A PATIENT AND BLOCKING A SUBSEQUENT SALE OF A DRUG CONTRAINDICATED FOR THE HEALTH CONDITION

(75) Inventor: Thomas P. Lawlor, Chicago, IL (US)

(73) Assignee: Walgreen Co., Deerfield, IL (US)

( * ) Notice: Subject to any disclaimer, the term of this patent is extended or adjusted under 35 U.S.C. 154(b) by 686 days.

(21) Appl. No.: 12/129,147

(22) Filed: May 29, 2008

(51) Int. Cl.
*G66Q 50/00* (2006.01)
(52) U.S. Cl. .................................. 705/3; 705/2; 600/300
(58) Field of Classification Search .................. 705/2, 3; 600/300
See application file for complete search history.

(56) References Cited

U.S. PATENT DOCUMENTS

2002/0143582 A1* 10/2002 Neuman et al. .................... 705/3
2006/0129433 A1* 6/2006 Koneru ............................. 705/3
2008/0162352 A1* 7/2008 Gizewski ........................ 705/50

* cited by examiner

*Primary Examiner* — Lena Najarian
(74) *Attorney, Agent, or Firm* — Francis C. Kowalik; Marshall, Gerstein & Borun LLP; Randall G. Rueth

(57) ABSTRACT

A system and method for inferring a possible pregnancy based on a first filled prescription and blocking the sale of a second prescription for a drug contraindicated for pregnancy is disclosed. First prescription information may be received and a possible pregnancy of the patient may be inferred. An association of the inferred possible pregnancy and the patient may be retained for a given length of time. When second prescription information is received, a check for the association may be made. If an association exists, the filling and the sale of the second prescription may be blocked. The block of the sale of the second prescription may be overridden.

20 Claims, 4 Drawing Sheets

METHOD OF INFERRING A HEALTH CONDITION BASED ON A PRESCRIPTION FILLED FOR A PATIENT AND BLOCKING A SUBSEQUENT SALE OF A DRUG CONTRAINDICATED FOR THE HEALTH CONDITION

FIELD AND BACKGROUND OF THE DISCLOSURE

1. Field of the Disclosure

This disclosure generally relates to methods and systems for inferring a health condition of a patient based on a prescription, and blocking a subsequent sale of a drug contraindicated for the health condition prescribed for the patient.

2. Background Description

When a patient requests to fill a prescription, current standard business practice has the pharmacist or other filling entity check to see if the prescribed drug is contraindicated for certain health conditions. If the drug is contraindicated for a specific health condition, the pharmacist or filling entity typically asks the patient a screening question regarding the health condition before continuing with the filling and sale of the prescription. For instance, suppose a patient requests a pharmacy to fill a prescription for Arthrotec, a known teratogen and contraindicated for pregnancy. Upon receiving the prescription, the pharmacist or filling entity determines that Arthrotec is contraindicated for pregnancy and asks if the patient is pregnant. If the answer is positive, the filling and sale of the Arthrotec prescription is blocked, pending consultation with the patient's medical authorities. If the answer is negative, the pharmacist continues with the filling and sale of Arthrotec prescription.

A problem arises if the patient responds negatively to the pharmacist's questions, but is (perhaps unknowingly) incorrect. For instance, if a patient is taking fertility drugs and attempting to become pregnant, she may answer "not pregnant" in response to the pharmacist's question when in actuality, she is pregnant but does not yet know it. In such a case, filling the Arthrotec prescription and allowing its sale and eventual ingestion may result in potential miscarriage, abnormal fetal development, possible severe birth defects or other adverse and undesirable effects.

A method and a system are needed to further safeguard against the sale of contraindicated prescription drugs to patients that may possibly have a health condition for which the prescribed drugs are contraindicated.

BRIEF SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

As used herein, the term "pharmaceutical entity" is meant to include any entity or system authorized to receive prescriptions, for example, a store-front pharmacy, a pharmacy located as a department within a larger retail store-front, a pharmacy located in conjunction with a medical facility, and the like. A pharmaceutical entity may also be a non-bricks-and-mortar establishment, such as mail-order, phone-in, fax-in, or website able to receive and fill or direct the filling of prescriptions. "Pharmaceutical entity" may refer to any pharmaceutical entity authorized to receive prescriptions and/or coordinate the filling of the prescriptions. A pharmaceutical entity may fill the received prescriptions on-site, or it may direct or coordinate with a separate entity to perform the actual filling, such as when a prescription is received at a website and the filling instructions are sent to be executed at a warehouse or at a local pharmacy store-front physically proximate to the patient's residence or workplace.

Furthermore, as used herein, the term "pharmaceutical professional" is meant to include any person or persons employed by any known pharmaceutical entity or system that is responsible for at least a part of the ordering and filling process. The term "pharmaceutical professional" as used herein may also include an electronic step of the prescription ordering and/or filling process. For example, if a patient accesses a website to fill a prescription, the website or "pharmaceutical professional" may be programmed to prompt the patient with questions regarding pregnancy or other health conditions, to determine contraindication, to receive payment, and to perform any other steps associated with the receiving and filling of prescriptions.

The instant disclosure provides an embodiment of a method of inferring a possible pregnancy of a patient based on a prescription filled for a patient and blocking a subsequent sale of a drug contraindicated for pregnancy. When a patient brings a first prescription to be filled, the first prescription information may be received at the pharmaceutical entity. The first prescription information may include standard information known in the art, such as the name of the patient, a first drug identifier, the dosage amount and instructions, an identification and signature of the issuing medical authority, etc.

When the first prescription is for a pre-natal or fertility drug, a possible pregnancy of the patient may be inferred. Pre-natal drugs may typically be pre-natal vitamins but may also be other types of prescribed pre-natal drugs. Fertility drugs may include, for instance, clomiphene, gonadotropins, bromocriptine, or any other types of fertility drugs. Any type of pre-natal or fertility drug may be used with the embodiment method of the instant disclosure. Based on the received first drug identifier in the first prescription information, the possible pregnancy of the patient may be inferred.

An association may be made between the inferred possible pregnancy and the patient, and this association may be stored. The association may be stored in records or history maintained by the pharmaceutical entity. The records may be paper or electronic. They may be stored on-site, for instance, in a filing system, local database, or networked data storage mechanism. They may be electronically stored as a individual data field, a flag or bit associated with a record, a linkage or other type of indication. They may be stored remotely at a website or remotely networked data storage mechanism. Any known method for keeping pharmaceutical records may be used in accordance with the instant disclosure. Note that whether or not the patient is actually pregnant is not a concern of the method provided by the present disclosure. The present disclosure is directed to help safeguard against potential miscarriage, abnormal fetal development, birth defects and other types of adverse effects, and thus the embodiment errs on the conservative side by inferring a possible (as opposed to actual) pregnancy of the patient.

The association between the inferred possible pregnancy and the patient may be retained for a given duration of time. This duration of time may be pre-set to a default value, or it may be entered and/or changed with each new association. The duration of time may vary depending on the type of drug identified in the first prescription, or it may vary depending on one or more other parameters such as patient age, recommendation of medical authority, legal requirement(s) or other parameters. Upon expiration of the duration of time, the association may be automatically or manually removed, canceled, invalidated or other such action from the record.

Next, the embodiment provides for receiving a second, subsequent prescription for the patient where the second prescribed drug is contraindicated for pregnancy. The second prescription may be received using any of the methods described above for receiving the first prescription. The second prescription may contain second prescription information similar to the first prescription information, including a second drug identifier. The second drug identifier may be determined to be contraindicated for pregnancy using any method known in the art, such as (but not limited to) looking up contraindications in a table, book, database or other such manual or electronic data repository, or relying on a computer program or knowledge of a pharmaceutical professional.

Upon reception of the second prescription and the identification of the contraindicated second drug, a check is made for a retained association of the patient and a possible pregnancy. The check may typically be made by consulting the records or history maintained by the pharmaceutical entity. The check may be made manually or electronically by a computer or a pharmaceutical professional. If an association exists, the sale of the second prescription may be blocked. The sale may be blocked by a human pharmaceutical professional, for instance, by not ringing up the sale. If the pharmaceutical entity is a non-bricks-and-mortar entity such as a website, the sale may be blocked automatically by the pharmaceutical professional, for instance, by providing a pop-up indicating that the sale is blocked and not allowing further data to be entered.

The embodiment of the method may also provide for the blocking to be overridden. For instance, after the block of the sale of the contraindicated drug, if a patient obtains subsequent medical authorization to fill the second prescription even though a possible pregnancy may exist, the pharmaceutical professional may override the blocking and allow the second prescription to be filled and sold. A record of the override may be maintained in the pharmaceutical records. The entering of the override may require one or more pieces of information to be stored with the record of the override, such as any medical authorization(s), a waiver signed by the patient, or other such records. The entering of the override may be security-enabled, for instance, when only certain pharmaceutical professionals are enabled to enter an override via password protection or other security means. The override may be retained for a given duration of time, similar to the retention of the association indication of the patient and a possible pregnancy.

Further, the present application also provides an embodiment of a method for inferring a possible health condition based on a prescription filled for a patient and blocking the subsequent sale of a drug contraindicated for the health condition. When a patient brings a first prescription to be filled, the first prescription information may be received at the pharmaceutical entity. The first prescription information may include standard information known in the art, such as the name of the patient, a first drug identifier, the dosage amount and instructions, the medical authority that prescribed the first drug, etc.

A possible health condition may be inferred from the first drug identified by the first prescription information. For example, a possible pregnancy may be inferred from a prenatal or fertility drug prescription. A possible heart condition may be inferred from prescriptions for drugs such as calcium channel blockers, alpha- and beta-blockers, nitrates, statins and the like. Possible diabetes may be inferred from an insulin prescription. Other possible health conditions may also be inferred based on the first drug identifier of the first prescription information.

An association may be made between the inferred possible health condition and the patient, and this association may be stored. The association may be stored in records or history maintained by the pharmaceutical entity. The records may be paper or electronic. They may be stored on-site, for instance, in a filing system, local database, or networked data storage mechanism. They may be stored remotely at a website or remotely networked data storage mechanism. Any known method for keeping pharmaceutical records may be used in accordance with this embodiment.

The association between the inferred possible health condition and the patient may be retained for a given duration of time. This duration of time may be pre-set to a default value, or it may be entered and/or changed with each new association. The duration of time may vary depending on the name or type of drug of the first prescription, or it may vary depending on one or more other parameters such as patient age, recommendation of medical authority, legal requirement(s) or other parameters. Upon expiration of the duration of time, the association may be automatically or manually removed, canceled, invalidated or other such action from the record.

Multiple associations for multiple possible health conditions may be maintained for a single patient. For instance, if a patient is prescribed to be taking pre-natal vitamins, an association of the patient with a possible pregnancy may be retained. If the patient is further prescribed to be taking insulin, a separate association of the patient with possible diabetes may also be retained.

Next, the embodiment of the method provides for receiving a second prescription for the patient where the second prescribed drug is contraindicated for the possible health condition. The second prescription may be received using any of the methods described above for receiving the first prescription. The second prescription may contain second prescription information similar to the first prescription information, including a second drug identifier. The second drug identifier may be determined to be contraindicated for the possible health condition using any method known in the art, such as (but not limited to) looking up contraindications in a table, book, database or other such manual or electronic data repository, or relying on a computer program or knowledge of a pharmaceutical professional.

Upon reception of the second prescription and the identification of the second drug as being contraindicated for the health condition, ac heck is made for a retained association of the patient and the possible health condition. The check may typically be made by consulting the records or history maintained by the pharmaceutical entity. The check may be made manually or electronically by a computer or a pharmaceutical professional. If an association exists, the sale of the second prescription may be blocked. The sale may be blocked by a human pharmaceutical professional, for instance, not ringing up the sale. If the pharmaceutical entity is a non-bricks-and-mortar entity such as a website, the sale may be blocked automatically by the pharmaceutical professional, for instance, by providing a pop-up signifying that the sale is blocked and not allowing further data to be entered.

The embodiment of the method may provide for the block of the contraindicated drug to be overridden. For instance, after the block, if a patient obtains subsequent medical authorization to fill the second prescription in spite of the possible health condition, the pharmaceutical professional may override the block and allow the second prescription to be filled and sold. A record of the override may be maintained in the pharmaceutical records. The entering of the override may require one or more pieces of information to be stored with the record of the override, such as any medical authorization (s), a waiver signed by the patient, or other such records. The entering of the override may be security-enabled, for instance, when only certain pharmaceutical professionals are enabled to enter an override via password protection or other security means. The override may be retained for a given duration of time, similar to that of the association indication of the patient and the possible health condition.

The present disclosure also provides an embodiment of an exemplary system for inferring a possible pregnancy of a patient based on a prescription filled for a patient and blocking the subsequent sale of a drug contraindicated for pregnancy. The system may include a computer that is programmable to receive and retain first prescription information, infer the possible pregnancy and retain an association of the possible pregnancy and the patient. The computer may also be programmable to block the subsequent sale of a second drug contraindicated for pregnancy identified in a second prescription for the patient. The system may be a stand-alone computer at a pharmaceutical entity, it may be attached to any known local or remote network to which the pharmaceutical entity has access, or it may be integrated into one or more elements of any known local or networked system of the pharmaceutical entity. The system may support the method described above for inferring a possible pregnancy of a patient based on a prescription filled for a patient and blocking the subsequent sale of a drug contraindicated for pregnancy.

Another embodiment of the system may support the embodiment of the method described above for inferring a possible health condition based on a prescription filled for a patient and blocking the subsequent sale of a drug contraindicated for the health condition. The system may be a stand-alone computer at a pharmaceutical entity, it may be attached to any known local or remote network to which the pharmaceutical entity has access, or it may be integrated into one or more elements of any known local or networked system of the pharmaceutical entity.

DETAILED DESCRIPTION OF THE PREFERRED EMBODIMENTS

Although the following text sets forth a detailed description of numerous different embodiments, it should be understood that the legal scope of the description is defined by the words of the claims set forth at the end of this patent. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term by limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 1:
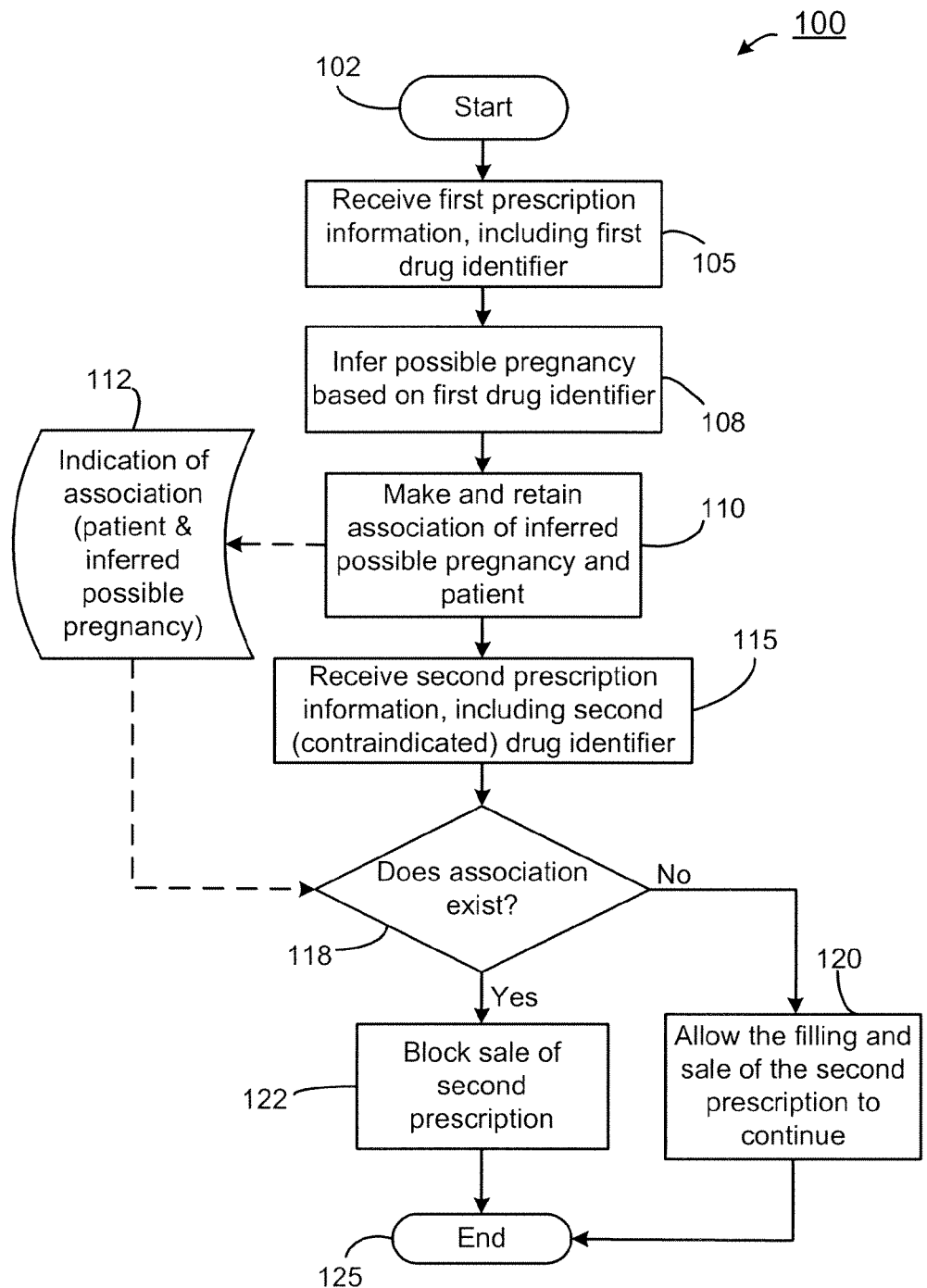
FIG. 1 illustrates an exemplary embodiment of a method of inferring a possible pregnancy based on a prescription filled for a patient and blocking the subsequent sale of a drug contraindicated for pregnancy.

FIG. 1 illustrates an exemplary embodiment of a method 100 for inferring a possible pregnancy based on a prescription filled for a patient and blocking the subsequent sale of a drug contraindicated for pregnancy. Method 100 may be used at a store-front pharmacy, where pharmacists, technicians and/or other pharmaceutical professionals receive and fill prescriptions. Alternatively, method 100 may be used by a mail-order, phone/fax order, website or other electronic prescription ordering and filling system. Method 100 may be used by any pharmaceutical entity authorized to receive prescriptions and coordinate the filling of the prescriptions. As previously discussed, the term "pharmaceutical entity" as used herein is meant to include any entity or system authorized to receive prescriptions, for example, a store-front pharmacy, a pharmacy located as a department within a larger retail store-front, a pharmacy located in conjunction with a medical facility, and the like. A pharmaceutical entity may also be a non-bricks-and-mortar establishment, such as mail-order, phone-in, fax-in, or website able to receive and fill or direct the filling of prescriptions.

As also previously discussed, the term "pharmaceutical professional" as used herein is meant to include any person or persons employed by any known prescription ordering and filling entity or system who are responsible for at least a part of the ordering and filling process. The term "pharmaceutical professional" as used herein may also include an electronic step of the prescription ordering and filling process. For example, if a patient accesses a website to fill a prescription, the website or "pharmaceutical professional" may be programmed to prompt the patient with questions regarding pregnancy or other health conditions, to determine contraindication, to receive payment, and to perform any other steps associated with the receiving and filling of prescriptions.

At the start 102 of method 100, first prescription information may be received (block 105), including a first drug identifier corresponding to the prescribed drug of the first prescription. The first drug identifier may be a brand or generic name, it may be a chemical compound, or it may be some other type of identifier. Other prescription information, such as dosage, ingestion interval, length of prescription, identification and signature of the issuing medical professional, patient name, and the like may also be received with the first prescription information. The first prescription may be received via a paper prescription handed to a store-front pharmaceutical professional; it may be received via an electronic order over a computer link or download via a network transmission, website access, email or other data transfer mechanism; or it may be received via mail delivery or a phone/fax order. Any known method of receiving communication regarding a prescription to be filled may operate in accordance with the instant disclosure.

Next, a possible pregnancy of the patient may be inferred from the first drug identifier (block 108). For instance, if the first drug identifier corresponds to a pre-natal prescription such as pre-natal vitamins or other pre-natal drugs, a possible pregnancy may be inferred. Alternatively, if the first drug identifier corresponds to a fertility prescription such as an estrogen antagonist, gonadotropin or other type of fertility drug, a possible pregnancy may be inferred. Note that the inferred possible pregnancy need not be an accurate assessment of an actual pregnancy. The present disclosure is intended to help safeguard against possible miscarriage, birth defects and other adverse health effects that may occur if a drug contraindicated for pregnancy is taken by a pregnant patient. Thus, method 100 errs on the conservative side by inferring a possible pregnancy.

An association of the patient and the possible pregnancy is then made and retained (block 110). An indication of this association may be retained in pharmaceutical records, files, or some other data storage area (block 112). The records/files may be paper or electronic. They may be electronically stored as a individual data field, a flag or bit associated with a record, a linkage or other type of indication. They may be maintained on-site or remotely. Any known method of storing pharmaceutical data and/or maintaining pharmaceutical records may operate in accordance with this disclosure. The association indication may be retained in the records/files for a given length of time. This length of time may be pre-determined or entered with the association indication, and may be able to be modified at any time.

At some time thereafter, a second, subsequent prescription may be received for the patient identifying a drug that is contraindicated for pregnancy (block 115). The second drug identifier may be a brand or generic name, it may be a chemical compound, or it may be some other type of identifier. Other prescription information, such as dosage, ingestion interval, length of prescription, identification and signature of the issuing medical professional, patient name, and the like may also be received with the second prescription information. The second prescription information may be received in a manner similar to the reception of the first prescription information. The determination of second drug identifier's contraindication may be made using any known method, including look-up tables or lists, accessing a website or other database, a modifier attached to the drug identifier in a downloaded database, reliance on the knowledge of a pharmaceutical professional, and the like. Any known method in the art of determining drug contraindication may be used in accordance with this disclosure.

Upon reception of the second prescription (block 115), a check for a possible pregnancy of the patient may be made (block 118) by searching for a retained association indication (block 112). If a retained association indication 112 is not found at block 118, the filling and sale of the second prescription may be allowed to continue (block 120). If a retained association indication 112 of the patient and a possible pregnancy is found at block 118, the sale of the contraindicated drug may be blocked (block 122) and the second prescription may not be filled. The method then may end (block 125).

At this point, after the blocking of the sale of the contraindicated drug, the pharmaceutical professional may take steps to interface with the patient and/or the medical professional (s) who prescribed the contraindicated drug to resolve the matter. With the authorization of one or more medical authorities, the blocking of the sale of the contraindicated drug may be overridden and the association indication removed. Such an override may be retained in the patient's pharmaceutical records/files.

One of ordinary skill in the art will appreciate that method 100 need not be limited to a health condition of possible pregnancy. Method 100 may be easily extended to apply to any health condition for which there are contraindicated drugs. For instance, a stomach ulcer condition may be inferred from a first prescription (block 108), and drugs contraindicated for stomach ulcers (for example, non-steroidal anti-inflammatory drugs or blood thinners) may be blocked from being sold (block 122). Another example may be a liver disease condition being inferred from a first prescription (block 108), and drugs contraindicated for liver disease (e.g., atorvastatin calcium to treat high cholesterol, amiodarone to regulate ventricular rhythm, among others) may be blocked from being sold (block 122). Inferring health conditions (block 108) instead of or in addition to pregnancy, and blocking respective corresponding contraindicated drugs (block 122) may use the method 100.

Multiple associations 112 for multiple possible health conditions may be made and retained (block 110) for a single patient. For instance, if a patient is prescribed to be taking pre-natal vitamins, an association 112 of the patient with a possible pregnancy may be retained (block 110). If the patient is further prescribed to be taking insulin, a separate association 112 of the patient with possible diabetes may also be retained (block 110).

Figure 2:
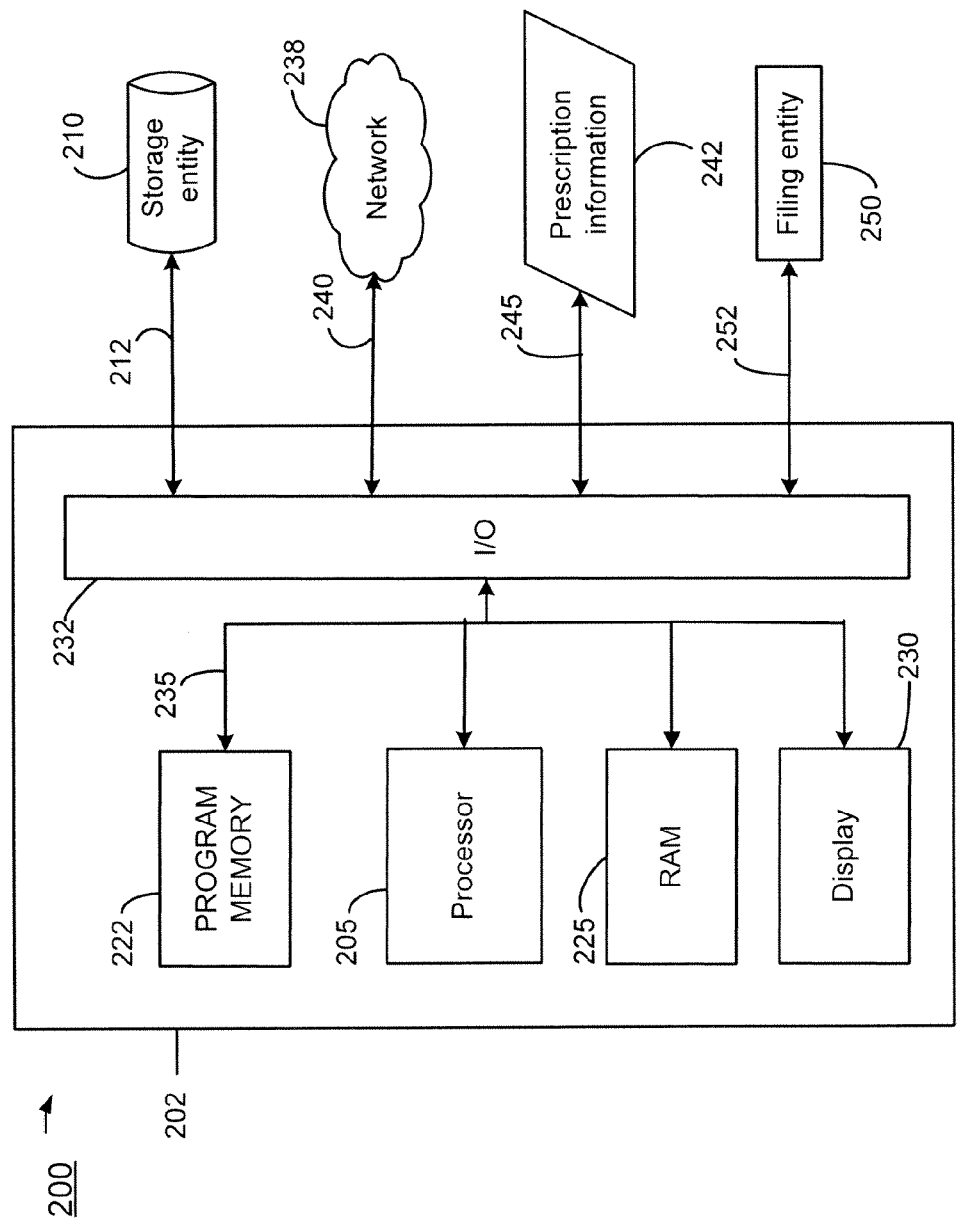
FIG. 2 is an embodiment of an exemplary system for inferring a possible pregnancy of a patient based on a prescription filled for a patient and blocking a subsequent sale of a drug contraindicated for pregnancy.

FIG. 2 illustrates an exemplary embodiment of a system 200 for inferring a possible pregnancy of a patient based on a prescription filled for a patient and blocking a subsequent sale of a drug contraindicated for pregnancy. For the sake of illustration, a simplified block diagram of a computer 202 is used to illustrate the principles of the instant disclosure. However, such principles apply equally to other electronic devices, including, but not limited to, cellular telephones, personal digital assistants, media players, appliances, gaming systems, entertainment systems, set top boxes, and automotive dashboard electronics, to name a few. The computer 202 may have a processor 205 that is operatively connected to a database or storage entity 210 via a link 212. Link 212 may be as simple as a memory access function, or it may be a wired, wireless, or multi-stage connection through a network. Many types of links are know in the art of networking and are possible.

The storage entity 210 may be contained in the same entity as the computer 202, or it may be a separate local or remote entity. Storage entity 210 may be a database on a computer, server or other electronic device or it may be a storage device such as a hard drive, disk, mass storage device, or the like. Many types of storage entities are known in the art of data storage and may operate with the disclosure of this application. It should be noted that, while not shown, additional, multiple databases/storage entities may be linked to the computer 202 in a known manner. The storage entity 210 may include any data that may be relevant to inferring a possible pregnancy of a patient based on a prescription filled for the patient and blocking a subsequent sale of a drug contraindicated for pregnancy, such as but not limited to pharmaceutical records, listings of contraindicated drugs, retention of associations of patients and possible pregnancies, etc. These and other types of relevant data relevant may be stored on a single storage entity 210 or across multiple storage entities 210.

Data stored in the storage entity 210 may be obtained by the computer 202 through a download, data transfer, or other such mechanism. Alternatively, the computer 202 may request or read the storage device 210 to obtain only the necessary data relevant to inferring a possible pregnancy of a patient based on a prescription filled for the patient and blocking the subsequent sale of a drug contraindicated for pregnancy.

The computer 202 may include a processor 205 (may be called a microcontroller or a microprocessor) for executing computer executable instructions, a program memory 222 for permanently storing data related to the computer executable instructions, a random-access memory (RAM) 225 for temporarily storing data related to the computer executable instructions, a display 230 and an input/output (I/O) circuit 232, all of which may be interconnected via an address/data bus 235. It should be appreciated that although only one microprocessor 205 is shown, the computer 202 may include multiple microprocessors 205. Similarly, the memory of the computer 202 may include multiple RAMs 225 and multiple program memories 222. Although the I/O circuit 232 is shown as a single block, it should be appreciated that the I/O circuit 232 may include a number of different types of I/O circuits. The RAM(s) 225 and program memories 222 may be implemented as semiconductor memories, magnetically readable memories, and/or optically readable memories, for example.

The computer 202 may also be operatively connected to a network 238 via a link 240. Similar to link 212, the form of link 240 may take any form known in the art of networking. Information from the storage entity 210 may be accessed by computer 202 via link 240 and the network 238.

The computer 202 may receive prescription information 242 over a link 245. Link 245 may be the same entity as network link 240 or database link 212, or it may be a separate entity. Link 245 may be an operator/user interface, for example, via a touch screen display 230 or keyboard (not pictured) of computer 202, or it may be a local or remote network connection to a server, website, other computer, or a different database. The computer 202 may receive a plurality of prescription information 242 from a plurality of sources, for example, when a single computer 202 receives prescription information 242 from multiple medical entities such as doctors' offices, hospitals, and the like. In this case, multiple links 245 are possible.

The computer 202 may also be operatively connected to a filling entity 250 via a link 252. Link 252 may be the same entity as network link 240, database link 212 or prescription information link 245, or it may be a separate entity. Filling entity 250 may receive instructions from computer 202 and fill prescriptions according to the received instructions. Filling entities 250 may be automatic processes or systems, they may be manual or one or more physical persons, or some combination of the two. Multiple links 252 to multiple filling entities 250 may be possible. For example, a single computer 202 may host a website and receive a plurality of prescriptions for different patients from various locations across the country. The computer 202 may distribute filling instructions across multiple links 252 to multiple physical pharmacy store-fronts in proximity to the each patient's physical location, with each store-front having with its own filling entity 250. Another example may include linking to an automatic filling entity for one class of drugs, and linking to a manual filling entity for a different class of drugs. Other examples are also possible. Link 252 may be the same link as links 212, 240 or 245, or it may be a separate link. Link 252 may also be a local connection or a remote connection through network 238.

System 200 may support method 100 and additional methods of inferring a possible pregnancy of a patient based on a prescription filled for a patient and blocking a subsequent sale of a drug contraindicated for pregnancy.

Figure 3A:
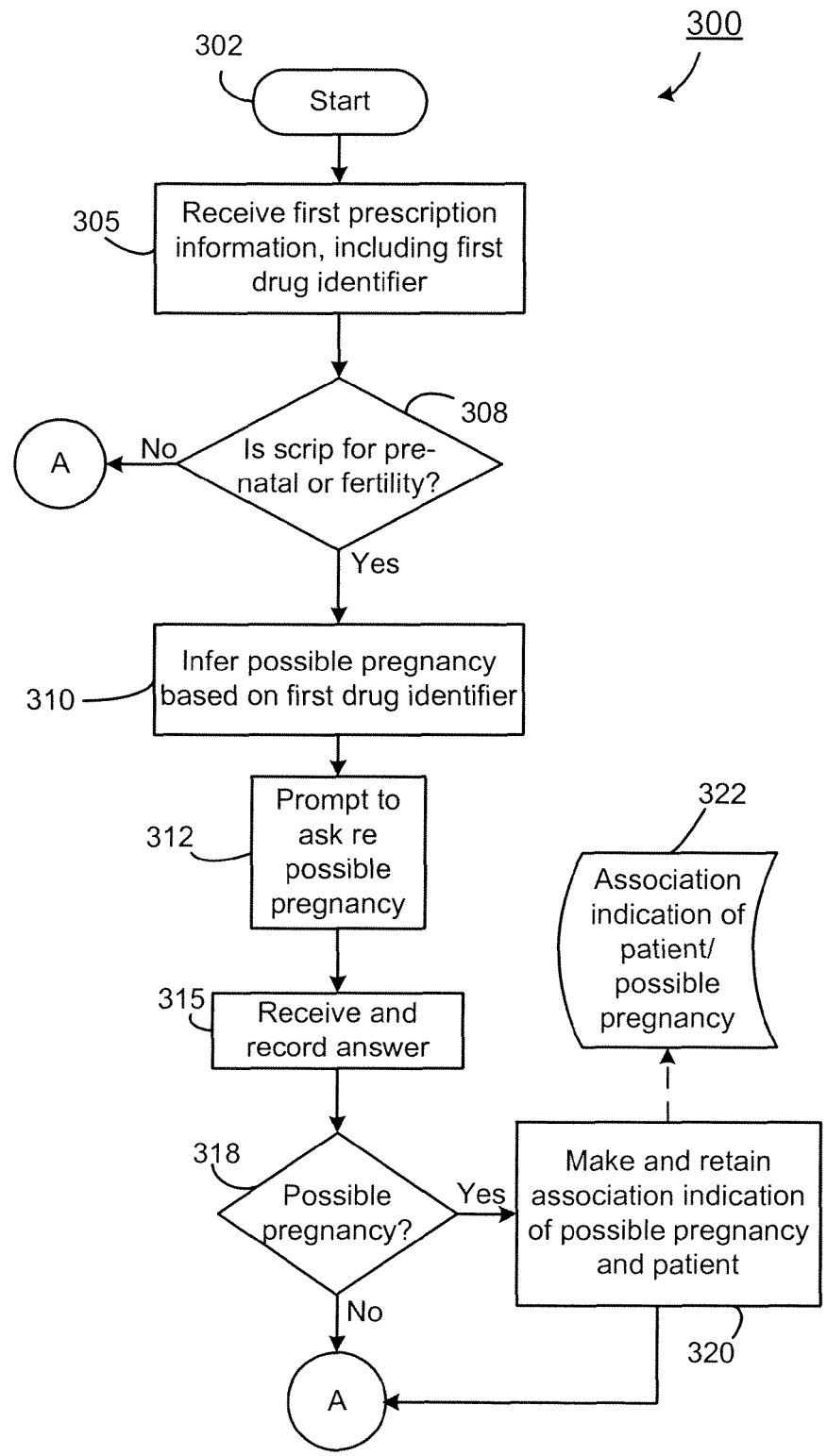
FIGS. 3a and 3b illustrate another embodiment of a method of inferring a possible health condition based on a prescription filled for a patient and blocking the subsequent sale of a drug contraindicated for the health condition.
Figure 3B:
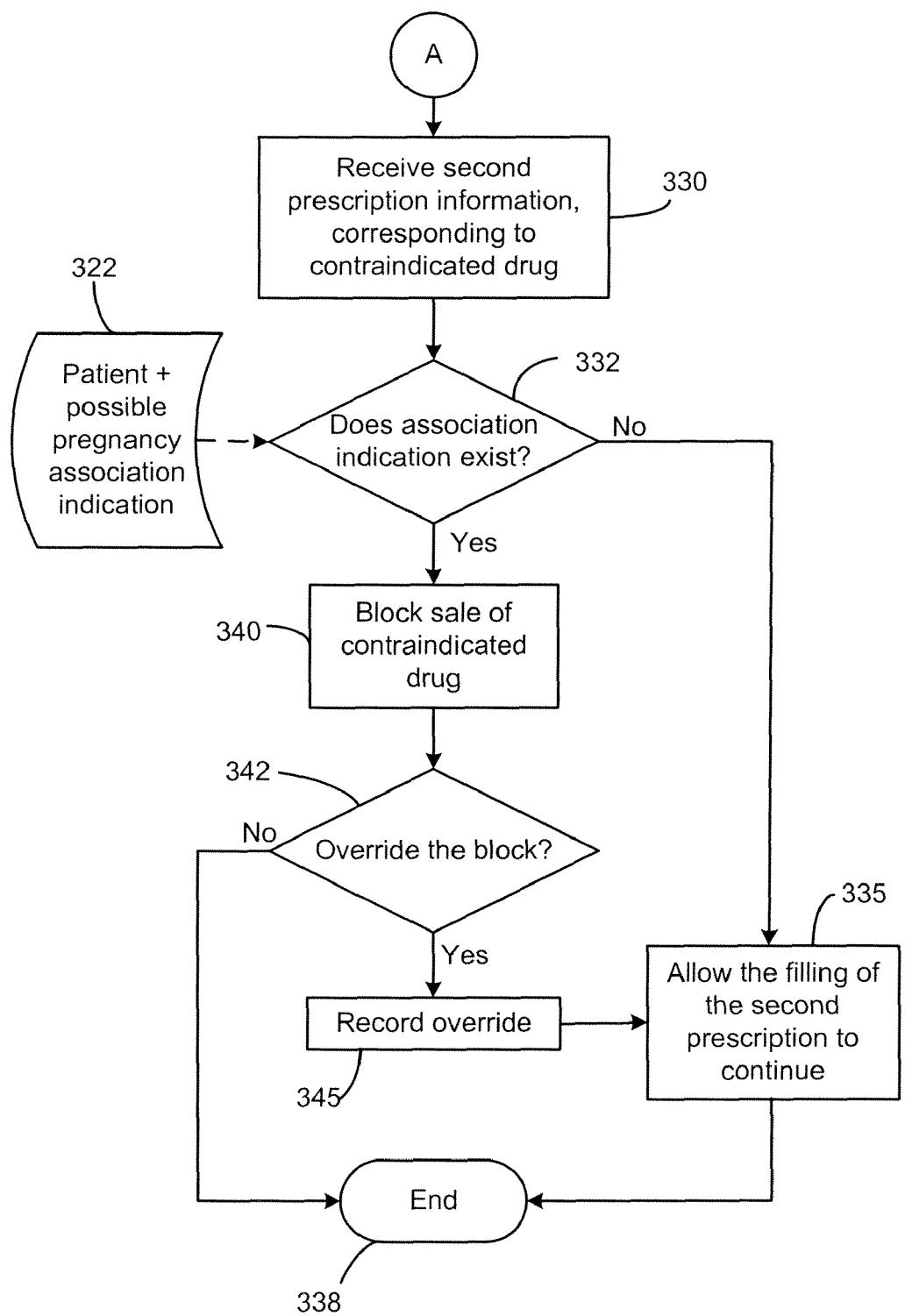

FIGS. 3a and 3b illustrate a more complex embodiment of a method 300 for inferring a possible pregnancy of a patient based on a prescription filled for a patient and blocking a subsequent sale of a drug contraindicated for pregnancy. For this embodiment, method 300 shall be discussed as operating in conjunction with system 200 of FIG. 2. However, one of ordinary skill in the art will recognize that method 300 is not limited to only operating in accordance with the embodiment of system 200. Method 300 may also operate in accordance with other embodiments of systems with differing levels and portions of manual and/or automated elements.

In FIG. 3a, at the start (block 302), computer 202 may receive first prescription information 242, including a first drug identifier, over link 245 (block 305). The first prescription information 242 may be received by user input via I/O circuit 232, such as when a pharmaceutical professional inputs the first prescription information 242 from a paper prescription or telephone order into a store-front pharmacy computer 202. Or, first prescription information 242 may be received over link 240 via network 238 via data transfer or download, email, data entered at a website, or some other electronic means. First prescription information 242 may be received at the store-front computer 202, a pharmaceutical website computer 202, a phone-order warehouse computer 202, or some other computer 202 associated with a pharmaceutical entity. In this case, link 240 and link 245 may be the same entity. Other ways of receiving first prescription information 242 over link 245 are also possible.

After receiving the first prescription information 242, the method 300 may check to see if the script is for a pre-natal or fertility drug (block 308). If the first drug identifier is not a pre-natal or a fertility drug as determined at block 308, no inference of possible pregnancy may be made, associated and/or retained. If the first prescription identifier is for a pre-natal or fertility drug as determined at block 308, a possible pregnancy may be inferred (block 310). Next, the system may then prompt the pharmaceutical professional to ask if the patient is possibly pregnant (block 312). The prompting may occur, for instance, by a pharmacy store-front computer 202 displaying on its screen 230 a prompt in a pop-up window for the pharmaceutical professional such as "There is a possible indication of pregnancy for this medication. Please verify if the patient is trying to, planning to, or currently pregnant?" Alternately, for example, if system 200 is not at a store-front but at a website, the website may display a similar query via display 230. Other embodiments of the prompting at block 312 may also be possible.

An answer regarding the possible pregnancy may be received and recorded (block 315), for instance, by the pharmaceutical professional entering the answer via display screen 230 or keyboard through the I/O circuit 232 into storage entity 210. Alternatively, using the website example, at block 315, the answer may be received via network 238 over link 240 and recorded into storage entity 210.

If, at block 318, the recorded answer indicates a possible pregnancy, an association between the patient and a possible pregnancy may be made and retained (block 320), and this association indication 322 may be sent over link 212 to be stored in storage entity 210. Storing the association indication 322 may be a simple write to a database 210 resident in computer 202, it may be a data transfer to a locally networked data storage area 210, or it may be a remote write over link 240 via network 238 to a remote storage entity 210. The association indication 322 may be electronically stored as a individual data field, a flag or bit associated with a record, a linkage or other type of indication. Alternatively, the association indication 322 may be stored in a "low-tech" storage entity 210 such as a written file or record.

The association indication 322 may also contain a duration of time of storage that specifies how long to keep the association indication 322. This duration of time may be determined a priori, or it may be input and/or modified by the pharmaceutical professional for each association indication 322. The duration of time may vary depending on the name or type of drug of the first prescription, or it may vary depending on one or more other parameters such as patient age, recommendation of medical authority, legal requirement(s) or other parameters. Upon expiration of the duration of time, the association may be automatically or manually removed, canceled, invalidated or other such action from the record.

One of ordinary skill in the art will note that method 300 may be implemented with different levels of safeguarding. A more conservative embodiment may always infer a possible pregnancy without prompting to ask if the patient is possibly pregnant, i.e., the method 300 may proceed from block 310 directly to block 320. A different level of safeguarding may occur where the prompting may take place as in block 312 and the answer may be received and recorded as in block 315. Independent of the received answer, however, the association indication 322 may always be created and retained (block 320), thus skipping decision block 318. Other embodiments with varying levels of safeguarding may also be implemented.

If, at block 318, the recorded answer indicates no possible pregnancy, the method 300 continues on to FIG. 3b. Continuing with method 300 in FIG. 3b, second prescription information may be received for the patient, the second prescription corresponding to a drug contraindicated for pregnancy (block 330). The second prescription information may be received in a manner similar to the reception of the first prescription information. Contraindication may be determined by any method known in the art, including using a table, book, chart or other database, relying on the knowledge of the pharmaceutical professional, or by other means. Any known method of determining drug contraindication may be used in accordance with this disclosure.

Next, a determination may be made of whether an existing association indication of the patient and a possible pregnancy exists (block 332). The determination may be made by consulting the storage entity 210 for an existing association indication 322. If an existing association indication 322 is not found at block 332, the patient may be assumed to be not possibly pregnant, and the filling of the second prescription may continue by sending instructions via link 252 to filling entity 250 (block 335). Filling entity 250 may be automatic, manual, or some combination of the two. Filling entity 250 may be co-located with computer 202, or it may be remote. The link 252 may be an electronic network link as described above, or alternatively, it may be a "low-tech" link such as printing, faxing, telephoning or even displaying instructions for a human pharmaceutical professional to follow for a manual filling of the prescription. Method 300 may operate in accordance with these and any known methods of communicating to a prescription filling entity 250. Lastly, at block 338, the method 300 may end.

If an existing association indication 322 is found at block 332, the sale of the contraindicated drug may be blocked (block 340). Blocking may be implemented in a variety of ways, from a "low-tech" refusal of a human pharmaceutical professional to fill the second prescription, to some degree of automation such as the local computer or website 202 displaying a message on its screen 230, for example, "Pregnancy is an absolute contraindication for Drug X. Physician approval required before sale may be continued." Other ways of blocking the sale of the contraindicated drug may also be possible.

After the blocking of the sale of the contraindicated drug at block 340, a consultation with the issuers of the patient's first and second prescriptions may occur. The consultation may result in an override of the block of the sale, that is, the patient may be allowed by her medical professional(s) to fill the second prescription for the contraindicated drug. An override may be authorized by the one or more medical professionals of the patient, for example, if a patient has stopped trying to become pregnant, has had a negative pregnancy test, or if the health issue for which the contraindicated drug is prescribed is deemed to be critical to her health. If a block override is received as determined at block 342, the override may be recorded along with any pertinent information such as the authorization(s) of the medical professional(s), date(s) of consultation, a waiver signed by the patient, and the like (block 345). The entering of the override may be security-enabled, for instance, when only certain pharmaceutical professionals are enabled to enter an override via password protection or other security means. The override may be retained for a given duration of time, similar to that of the association indication of the patient and the possible health condition. The second prescription for the contraindicated drug may then continue to be filled (block 335), and the method 300 may end (block 338).

If a block override is not received as determined in block 342, then the sale of the contraindicated drug identified in the patient's second prescription may continue to be blocked, and the method 300 may end (block 338).

Alternative embodiments of method 300 with varying levels of restriction may be implemented. For instance, a more conservative embodiment may prohibit overrides altogether, and may proceed from block 340 directly to the end of the method 300. Or, in a different embodiment, an additional step may be added such that if an override is received and recorded at block 345, the method 300 may continue filling the second prescription at block 335 only if association indication 322 of the patient and possible pregnancy is removed. Other embodiments may include a password or other electronic authorization in order to record an override of the block 345, for instance, reflecting a subset of pharmaceutical professionals who are authorized to enter overrides.

One of ordinary skill in the art will appreciate that method 300 need not be limited to a health condition of possible pregnancy. Method 300 may be easily extended to apply to any health condition for which there are contraindicated drugs. For instance, a heart condition may be inferred from a first prescription (block 305), and drugs contraindicated for the inferred heart condition may be blocked from being sold (block 340). Another example may be a liver disease condition being inferred from a first prescription (block 305), and drugs contraindicated for liver disease may be blocked from being sold (block 340). Inferring health conditions (block 310) instead of or in addition to pregnancy, and blocking respective corresponding contraindicated drugs (block 340) may use the method 300.

Multiple associations 322 for multiple possible health conditions may be made and retained (block 320) for a single patient. For instance, if a patient is prescribed to be taking pre-natal vitamins, an association 322 of the patient with a possible pregnancy may be retained (block 320). If the patient is further prescribed to be taking insulin, a separate association 322 of the patient with possible diabetes may also be retained (block 320).

Although the foregoing text sets forth a detailed description of numerous different embodiments, it should be understood that the scope of the patent is defined by the words of the claims set forth at the end of this patent. The detailed description is to be construed as exemplary only and does not describe every possible embodiment because describing every possible embodiment would be impractical, if not impossible. Numerous alternative embodiments could be implemented, using either current technology or technology developed after the filing date of this patent, which would still fall within the scope of the claims.

Thus, many modifications and variations may be made in the techniques and structures described and illustrated herein without departing from the spirit and scope of the present claims. Accordingly, it should be understood that the methods and apparatus described herein are illustrative only and are not limiting upon the scope of the claims.

What is claimed:

1. A method, in a networked computer system of a pharmacy system, for inferring a possible pregnancy of a patient and blocking a sale of a drug contraindicated for pregnancy, comprising:
    receiving, at a computer included in the networked computer system of the pharmacy system, first prescription information corresponding to a first prescription corresponding to the patient, the computer being operatively connected to a filling entity that is included in the networked computer system of the pharmacy system, the filling entity being configured to fill the first prescription and a second prescription, the first prescription consisting of one of a pre-natal prescription or a fertility prescription, and the first prescription information including a first drug identifier;
    automatically inferring, at the computer, the possible pregnancy based on the first drug identifier;
    storing an association of the inferred possible pregnancy and the patient in a remote database included in the networked computer system of the pharmacy system;
    causing, by the computer, the filling entity to fill the first prescription;
    receiving, in the networked computer system of the pharmacy system, second prescription information corresponding to the second prescription, the second prescription to be filled for the patient and including a second drug identifier corresponding to the drug contraindicated for pregnancy; and
    performing an automated check for the stored association, and, if the stored association exists, blocking the sale of the drug contraindicated for pregnancy, including preventing the second prescription from being filled by the filling entity.

2. The method of claim 1, further comprising overriding the blocking of the sale of the drug contraindicated for pregnancy, including causing the filling entity to fill the second prescription and completing a sale of the second prescription.

3. The method of claim 2, wherein overriding the blocking of the sale of the drug contraindicated for pregnancy is performed after receiving an authorization from a medical authority.

4. The method of claim 2, further comprising storing a record of the override in the remote database.

5. The method of claim 1, further comprising automatically generating a prompt to ask a question regarding the inferred possible pregnancy, and wherein the association is stored if an indication of inferred possible pregnancy is received in response to the question.

6. The method of claim 1, further comprising:
    retaining, in the remote database, the association of the inferred possible pregnancy and the patient for a specified length of time, wherein the specified length of time is based on at least one of: a type of drug of the first prescription, an age of the patient, or a legal requirement; and
    removing the association from the remote database upon after the specified length of time has passed.

7. A computer system, corresponding to a pharmacy system, for automatically inferring a possible pregnancy of a patient and blocking a sale of a drug contraindicated for pregnancy, comprising:
    a first set of prescription information corresponding to a first prescription corresponding to a patient, including a first drug identifier, the first set of prescription information received at the computer system corresponding to the pharmacy system from another medical entity via a link included in the computer system;
    a second set of prescription information corresponding to a second prescription to be filled for the patient, including a second drug identifier corresponding to the drug contraindicated for pregnancy,
    a filling entity included in the computer system and configured to fill the first prescription and the second prescription, and
    a computer that is operatively connected to the filling entity and programmed to:
        receive and retain the first set of prescription information,
        cause the filling entity to fill the first prescription,
        automatically infer the possible pregnancy based upon the first drug identifier,
        retain an association of the inferred possible pregnancy and the patient in a remote database included in the computer system and remotely networked to the computer,
        receive the second set of prescription information, and
        block the sale of the drug contraindicated for pregnancy based on the retained association, including preventing the second prescription from being filled by the filling entity.

8. The computer system of claim 7, wherein the first prescription is one of a pre-natal prescription or a fertility prescription.

9. The computer system of claim 7, wherein the computer is further programmed to:
    automatically generate a prompt to ask a question regarding the inferred possible pregnancy and receive a response to the asked question, and wherein the association is retained if an indication of the inferred possible pregnancy is received via the response.

10. The computer system of claim 7, wherein:
    the association of the inferred possible pregnancy and the patient is automatically retained in the remote database for a specified length of time,
    the specified length of time is based on at least one of: a type of drug of the first prescription, an age of the patient, or a legal requirement;
    the specified length of time is modifiable; and
    the association is automatically invalidated after the specified length of time has passed.

11. The computer system of claim 7, where the computer is further programmed to override the blocking of the sale of the drug contraindicated for pregnancy, retain a record of the override, cause the filling entity to fill the second prescription, and complete a sale of the second prescription.

12. A method, in a computer system of a pharmacy system, for inferring a possible health condition of a patient and blocking a sale of a drug contraindicated for the possible health condition, comprising:
   receiving, at a computing device of the computer system of the pharmacy system, first prescription information corresponding to a first prescription corresponding to the patient, the first prescription information including a first drug identifier, the computing device being in operative connection with a prescription filling entity included in the computer system, and the prescription filling entity being configured to fill the first prescription;
   automatically inferring, by execution of computer-executable instructions stored at the computing device, the possible health condition based on the first drug identifier;
   automatically generating, by execution of the computer-executable instructions, a prompt to ask a question regarding the inferred possible health condition;
   storing, by the computing device in a storage entity that is included in the computer system and that is remotely accessible to the computing device, an association of the inferred possible health condition and the patient if an indication of the inferred possible health condition is received in response to the question;
   receiving, into the computer system, second prescription information corresponding to a second prescription to be filled for the patient, including a second drug identifier corresponding to the drug contraindicated for the possible health condition;
   checking, by execution of the computer-executable instructions, for the stored association and blocking the sale of the drug contraindicated for the possible health condition if the stored association exists, including preventing the prescription filling entity from filling the second prescription;
   overriding, by execution of the computer-executable instructions and based on an authorization of a medical authority, the blocking of the sale of the drug contraindicated for the possible health condition and instructing the prescription filling entity, by the computing device, to initiate a filling of the drug contraindicated for the possible health condition; and
   retaining, by the computing device in the storage entity, a record of the override.

13. The method of claim 12, wherein the inferred possible health condition is pregnancy.

14. The method of claim 12, wherein the first prescription is one of a pre-natal prescription or a fertility prescription.

15. The method of claim 12, further comprising storing, by the computing device in the storage entity, the association of the inferred possible health condition and the patient for a specified length of time.

16. The method of claim 12, wherein the inferred possible health condition is a liver condition.

17. The method of claim 12, wherein the inferred possible health condition is diabetes.

18. The method of claim 12, wherein:
   the possible health condition is a first possible health condition and the association is a first association; and
   the method further comprises:
      receiving, at the computing device of the computer system, third prescription information corresponding to a third prescription for the patient, including a third drug identifier;
      automatically inferring, by execution of computer-executable instructions stored at the computing device, a second possible health condition based on the third drug identifier;
      storing, by the computing device in the storage entity accessible to the computing device, an second association of the inferred second possible health condition and the patient; and
      checking, by execution of the computer-executable instructions, for the stored second association and blocking the sale of a drug contraindicated for the possible second health condition if the stored second association exists.

19. A networked computing system of a pharmacy system for inferring a possible health condition of a patient and blocking a sale of a drug contraindicated for the possible health condition, comprising:
   means for receiving, at a computer included in the networked computing system of the pharmacy system, first prescription information corresponding to a first prescription for the patient, the computer being operatively connected to a filling entity included in the pharmacy system, the filling entity being configured to fill the first prescription and a second prescription based on instructions from the computer, and the first prescription including a first drug identifier;
   means for automatically inferring the possible health condition based on the first drug identifier;
   means for automatically generating a prompt to ask a question regarding the inferred possible health condition;
   means for storing, in a remote database included in the networked computing system and communicatively connected to the computer, an association of the inferred possible health condition and the patient if an indication of the inferred possible health condition is received in response to the question;
   means for receiving, at the networked computing system, second prescription information corresponding to a second prescription to be filled for the patient, including a second drug identifier corresponding to the drug contraindicated for the possible health condition;
   means for checking for the stored association and blocking the sale of the drug contraindicated for the possible health condition if the stored association exists, including preventing the second prescription from being filled by the filling entity;
   means for overriding, based on an authorization of a medical authority, the blocking of the sale of the drug contraindicated for the possible health condition; and
   means for retaining a record of the override.

20. A method, in a networked computer system of a pharmacy system, for inferring a possible medical condition of a patient and blocking a sale of a drug contraindicated for the possible medical condition, comprising:
   receiving, at a computer included in the networked computer system of the pharmacy system, first prescription information corresponding to a first prescription corresponding to the patient, the computer being operatively connected to a filling entity that is included in the networked computer system of the pharmacy system, the filling entity being configured to fill the first prescription and a second prescription, and the first prescription information including a first drug identifier;

automatically inferring, at the computer, the possible medical condition based on the first drug identifier;
storing an association of the possible medical condition and the patient in a remote database included in the networked computer system of the pharmacy system;
causing, by the computer, the filling entity to fill the first prescription;
receiving, in the networked computer system of the pharmacy system, second prescription information corresponding to the second prescription, the second prescription to be filled for the patient and including a second drug identifier corresponding to the drug contraindicated for the possible medical condition; and
performing an automated check for the stored association, and, if the stored association exists, blocking the sale of the drug contraindicated for possible medical condition, including preventing the second prescription from being filled by the filling entity.

* * * * *